US007696311B2

(12) United States Patent
Han et al.

(10) Patent No.: US 7,696,311 B2
(45) Date of Patent: Apr. 13, 2010

(54) PROCESS AND SYSTEMS FOR RECOVERY OF PEPTIDES

(75) Inventors: Yeun-Kwei Han, Louisville, CO (US); Hiralal N. Khatri, Louisville, CO (US); Robert J. Topping, Longmont, CO (US)

(73) Assignee: Roche Colorado Corporation, Boulder, CO (US)

( * ) Notice: Subject to any disclaimer, the term of this patent is extended or adjusted under 35 U.S.C. 154(b) by 1021 days.

(21) Appl. No.: 11/021,845

(22) Filed: Dec. 23, 2004

(65) Prior Publication Data

US 2005/0165216 A1 Jul. 28, 2005

Related U.S. Application Data

(60) Provisional application No. 60/533,653, filed on Dec. 31, 2003.

(51) Int. Cl.
*A61K 38/00* (2006.01)
(52) U.S. Cl. .................. 530/333; 514/12; 514/13; 514/14; 514/15; 514/16; 514/17
(58) Field of Classification Search .............. None
See application file for complete search history.

(56) References Cited

U.S. PATENT DOCUMENTS

| 4,075,192 | A | * | 2/1978 | Nicolaides ........... 530/328 |
| 4,105,652 | A | | 8/1978 | Meienhofer et al. |
| 4,707,541 | A | | 11/1987 | Diaz et al. |
| 4,774,319 | A | * | 9/1988 | Ono et al. ........... 530/324 |
| 5,212,287 | A | | 5/1993 | Tolle et al. |
| 5,356,596 | A | | 10/1994 | Nokihara et al. |
| 5,464,933 | A | | 11/1995 | Bolognesi et al. |
| 5,656,480 | A | | 8/1997 | Wild et al. |
| 5,712,367 | A | | 1/1998 | Bernard et al. |
| 6,015,881 | A | | 1/2000 | Kang et al. |
| 6,281,331 | B1 | | 8/2001 | Kang et al. |
| 6,469,136 | B1 | | 10/2002 | Bray et al. |
| 6,479,055 | B1 | | 11/2002 | Bolognesi et al. |
| 2002/0132766 | A1 | | 9/2002 | DeGrado et al. |
| 2003/0125516 | A1 | | 7/2003 | Bray et al. |
| 2005/0143568 | A1 | | 6/2005 | Schwindt |
| 2005/0164912 | A1 | | 7/2005 | Bigelow et al. |
| 2005/0165215 | A1 | | 7/2005 | Bigelow et al. |
| 2005/0165216 | A1 | | 7/2005 | Han et al. |

FOREIGN PATENT DOCUMENTS

| WO | WO 99/48513 | 9/1999 |
| WO | WO 03/062266 | 7/2003 |

OTHER PUBLICATIONS

Chen et al. Effect of Hydrophobicity on Utilization of Peptides by Ruminal Bacteria In Vitro. Applied and Environmental Microbiology. Sep. 1987. vol. 53, No. 9, pp. 2021-2025.*
Riniker et al. (1993) Tetrahedron Letters 49:9307-9320.
Lloyd-Williams et al. (1993) Tetrahedron Letters 49:11065-11133.
Bray, Brian L. (Jul. 2003) Nature Review 2:587-593.
Andersson et al. (2000) Biopolymers 55:227-250.

* cited by examiner

*Primary Examiner*—Anish Gupta
*Assistant Examiner*—Marcela M Cordero Garcia
(74) *Attorney, Agent, or Firm*—Brian L. Buckwalter

(57) ABSTRACT

The invention provides methods of obtaining a peptide that include steps of synthesizing a peptide intermediate having one or more side chain protecting groups; providing a solvent to the peptide intermediate to form a peptide intermediate composition; and providing a precipitating agent in an amount sufficient to precipitate the peptide intermediate from the peptide intermediate composition, wherein the precipitating agent is an alcohol having three or more carbon atoms. Also provided are methods for precipitating peptides, methods for concentration peptides, and methods for filtering peptides.

18 Claims, No Drawings

PROCESS AND SYSTEMS FOR RECOVERY OF PEPTIDES

PRIORITY CLAIM

The present non-provisional patent Application claims priority under 35 USC §119(e) from U.S. Provisional Patent Application having Ser. No. 60/533,653, filed on Dec. 31, 2003, and titled PROCESS AND SYSTEMS FOR RECOVERY OF PEPTIDES, wherein said provisional patent application is commonly owned by the owner of the present patent application and wherein the entire contents of said provisional patent application is incorporated herein by reference.

FIELD OF THE INVENTION

The invention relates to synthesis of peptides. More particularly, the invention relates to recovery of peptide material via precipitation during synthesis.

BACKGROUND OF THE INVENTION

Many methods for peptide synthesis are described in the literature (for examples, see U.S. Pat. No. 6,015,881; Mergler et al. (1988) Tetrahedron Letters 29: 4005-4008; Mergler et al. (1988) Tetrahedron Letters 29: 4009-4012; Kamber et al. (eds), Peptides, Chemistry and Biology, ESCOM, Leiden (1992) 525-526; Riniker et al. (1993) Tetrahedron Letters 49: 9307-9320; Lloyd-Williams et al. (1993) Tetrahedron Letters 49: 11065-11133; Andersson et al. (2000) Biopolymers 55: 227-250; and Bray, Brian L. (July 2003) Nature Reviews 2: 587-593. The various methods of synthesis are distinguished by the physical state of the phase in which the synthesis takes place, namely liquid phase or solid phase.

Liquid phase methods (often referred to as solution phase methods) of synthesis carry out all reactions in a homogeneous phase. Successive amino acids are coupled in solution until the desired peptide material is formed. During synthesis, successive intermediate peptides are purified by precipitation and/or washes.

In solid phase peptide synthesis (SPPS), a first amino acid or peptide group is bound to an insoluble support, such as a resin. Successive amino acids are added to the first amino acid or peptide group until the peptide material of interest is formed. The product of solid phase synthesis is thus a peptide bound to an insoluble support. Peptides synthesized via SPPS techniques are then cleaved from the resin, and the cleaved peptide is isolated.

In addition to the liquid phase and SPPS techniques described above, a hybrid approach can be utilized. Hybrid synthesis is typically utilized to manufacture complex sequences. For example, in one representative hybrid scheme, complex sequences can be manufactured through the solid phase synthesis of relatively large, protected peptide intermediates, which are subsequently assembled either by solution phase or SPPS methods to produce a final peptide product. Thus, as a step in the synthesis, an intermediate compound is produced that includes each of the amino acid residues located in its desired sequence in the peptide chain with various of these residues having side chain protecting groups. The peptide intermediates are isolated, and the protected peptide intermediates are then coupled in solution to form a complete peptide. See, for example, WO 99/48513.

Peptides can also be manufactured utilizing recombinant techniques, whereby recombinant DNA technologies are utilized in cell-free systems to produce peptides of interest.

Peptides and amino acids from which peptides are synthesized tend to have reactive side groups as well as reactive terminal ends. When synthesizing a peptide, it is important that the amino group of one peptide reacts with the carboxyl group of another peptide. Undesired reactions at side groups or at the wrong terminal end of a reactant produces undesirable by-products, sometimes in significant quantities. These by-products and reactions can seriously impair yield or even ruin the product being synthesized from a practical perspective. To minimize side reactions, it is conventional practice to appropriately mask reactive side groups and terminal ends of reactants to help ensure that the desired reaction occurs.

For example, a typical solid phase synthesis scheme involves attaching a first amino acid or peptide group to a support resin via the carboxyl moiety of the peptide or amino acid. This leaves the amino group of the resin-bound material available to couple with additional amino acids or peptide material. Thus, the carboxyl moiety of the additional amino acid or peptide desirably reacts with the free amino group of the resin-bound material. To avoid side reactions involving the amine group of the additional amino acid or peptide, such amine group is masked with a protecting group during the coupling reaction. Two well-known amine protecting groups are the BOC group and the Fmoc group. Many others have also been described in the literature. After coupling, the protecting group on the N-terminus of the resin-bound peptide can be removed, allowing additional amino acids or peptide material to be added to the growing chain in a similar fashion. In the meantime, reactive side chain groups of the amino acid and peptide reactants, including the resin-bound peptide material as well as the additional material to be added to the growing chain, typically remain masked with side chain protecting groups throughout synthesis.

After synthesis, some or all of the protecting groups can be removed from the peptide product (deprotection). When substantially all protecting groups (terminal protecting groups and side chain protecting groups) are removed, this is referred to as global deprotection. Deprotection can occur contemporaneously with cleaving or can be carried out later if the peptide is to be further processed, modified, coupled to additional peptide or other material, and the like. Some cleaving reagents not only cleave peptide from the support resin, but also cause deprotection to occur at the same time (for example, the strongly acidic cleaving reagents associated with BOC chemistry). Other cleaving reagents are milder than those utilized in BOC chemistry and cleave without causing undue deprotection. The cleaved peptide remains substantially protected after cleaving as a result. The mildly acidic cleaving reagents associated with Fmoc chemistry tend to produce cleaved peptides in a protected state.

Peptide synthesis schemes typically require recovery of peptide material (for example, final peptide product or peptide intermediate) at one or more points during synthesis. For example, in SPPS synthesis methods, peptide material is typically recovered after it has been cleaved from the solid support. Similarly, in solution phase methods, the peptide material is recovered from solution. When peptide intermediates are synthesized and then coupled to produce a final, larger peptide product, as in hybrid approaches, several isolation steps may be required.

Typical methods to recover peptides involve the use of acid/salt chemistry. For example, peptide can be precipitated in aqueous salt (such as sodium chloride), and the solids can then be collected (for example, by vacuum filtration), washed, and dried. However, such methods present problems for commercial scale production, including high impurity levels. The presence of impurities in the solution with a peptide will result in downstream problems as well, if the peptide will be subsequently reacted with other species (such as additional peptides).

Other recovery methods involve concentration of the peptide solution under vacuum, followed by reconstitution with a solvent such as ethanol, methanol or heptane, then precipitation of the peptide by the addition of water. Known reagents used for peptide precipitation include heptane, water, methanol, ethanol, or diethyl ether. Each of these reagents has limitations. For example, some reagents can be extremely flammable, whereas other reagents can have a higher boiling point and therefore require higher temperatures during distillation steps to remove them. Further, the use of some reagents (such as heptane) during precipitation can cause electrostatic charge build up, which limits handling of this reagent. In addition, when the reagent is utilized only in the isolation steps, but not in other processing steps, specific equipment and/or processing steps (for example, to remove the reagent or purge the system) must be dedicated to the isolation steps involving that reagent.

As part of the recovery process, the precipitated peptide is collected, often by passing the composition containing the precipitated peptide through a filter. Characteristics of the precipitated peptide can impact the filterability of the precipitate. For example, the individual peptide particles that make up the peptide precipitate are desirably in a size range that allows for effective filtration of the precipitate. If outside this desirable size range, peptide precipitate can generate fines that clog the filtration apparatus (for example, when particles are too small) or become too tacky and prevent filtration (for example, when particles are too large).

For large-scale production of peptides, issues relating to product recovery and product purity, as well as reagent handling, storage and disposal, can greatly impact the feasibility of the peptide synthesis scheme. Thus, there is a continuing need for peptide synthesis processes capable of producing peptide materials of commercial interest in large batch quantities. Recovery of peptide material after synthesis, for example, by precipitation, is one aspect of the synthesis in which improvement is needed. Conventional methodologies may result in impurity levels that are higher than desirable.

SUMMARY OF THE INVENTION

The invention relates to methods for the recovery of peptide material (peptides and peptide intermediates) during synthesis, in particular methods involving recovering peptide material at excellent purity. According to the invention, an alcohol having three or more carbon atoms is used to precipitate peptide material from a composition. Preferably, the alcohol includes one or more secondary or tertiary hydroxyl groups. In preferred embodiments, the methods provide dramatically improved purity of peptide as compared to prior isolation techniques that utilize reagents such as heptane. Moreover, the methods can provide such improved purity in an efficient manner with respect to the number of isolation steps required and the total volume of reagents utilized.

In preferred embodiments, the inventive methods can provide improved purity of resulting peptide material, and, by way of consequence, improved final purification phases and improved yields of peptide. For example, in some embodiments, the inventive methods provide a 50% reduction of impurities in the peptide intermediate. Preferably, the inventive methods provide improved processing time, since washing and distillation steps can be eliminated.

According to the invention, one or more aspects of peptide recovery can be utilized to provide improved isolation of peptide material. In some aspects, improved purity of a peptide precipitate can be accomplished by selection of the precipitating agent. In other aspects, the amount of precipitating agent can be chosen to provide improved processability of a peptide precipitate. In still further aspects, the mixing energy can be controlled to impact processability of peptide material during isolation. These aspects can be utilized alone or in any combination to provide one or more of the advantages described herein.

According to some aspects, the invention involves selection of a precipitating agent to provide improved isolation of peptide material. The precipitating agent is preferably an alcohol having three or more carbon atoms and at least one hydroxyl group. In preferred embodiments, the alcohol is a secondary or tertiary alcohol. One preferred precipitating agent is isopropyl alcohol (IPA). Accordingly, the invention further relates to processes for large scale peptide synthesis wherein recovery of peptide material is accomplished utilizing isopropyl alcohol, thereby providing reagent cost savings, as well as decreased processing time. The decreased processing time can be achieved by reducing the number of isolation steps required for recovery of each peptide intermediate, as well as reducing the overall drying time. Further, isopropyl alcohol is utilized in other steps during peptide synthesis; therefore, use of this reagent for precipitation does not require additional dedicated reaction equipment or processing steps.

As discussed herein, processability of a peptide can be impacted by the amount of precipitating agent used, the amount of mixing energy used during isolation procedures, or both the amount of precipitating agent and mixing energy used during isolation procedures. In particular, one aspect of processability that can be impacted according to the inventive methods is the filterability of the peptide precipitate. In some preferred embodiments, the precipitating agent is used in an amount of at least 5 volumes per volume of reaction solution. In other embodiments, the precipitating agent is provided in an amount in the range of about 5 to about 8 volumes per volume of reaction solution, or in an amount in the range of about 6.5 to about 7.5 volumes of precipitating agent per volume of reaction solution. When used herein to describe the relative amount of precipitating agent, the volume of reaction solution is the total volume of reaction solution before the precipitating agent is added.

In one aspect of the invention, reagents and reactants can be used in lesser volumes to accomplish the same objectives as in typical synthetic methods. This can reduce overall raw material costs.

According to the invention, the mixing energy applied during recovery of a peptide can be controlled to provide improved methods and systems. In some embodiments, the mixing energy is in the form of agitation. Such agitation can be applied at a rate of less than about 2.5 m/s, or in the range of about 0.5 to about 2.5 m/s, or in the range of about 1 to about 2 m/s.

In one aspect, the invention provides a method of obtaining a peptide, comprising steps of: (a) synthesizing a peptide intermediate having one or more side chain protecting groups; (b) providing a solvent to the peptide intermediate to form a peptide intermediate composition; (c) providing a precipitating agent in an amount sufficient to precipitate the peptide intermediate from the peptide intermediate composition, wherein the precipitating agent comprises an alcohol having three or more carbon atoms.

In another aspect, the invention provides a method for precipitating a peptide comprising steps of: (a) providing a composition comprising a peptide intermediate having at least one side chain protecting group in a solvent; and (b) providing a precipitating agent to the composition, wherein the precipitating agent is an alcohol having three or more carbon atoms.

In yet another aspect, the invention provides a method for concentrating a peptide intermediate comprising steps of: (a) providing a composition comprising a peptide intermediate in a solvent comprising DCM; (b) precipitating the peptide intermediate by adding a precipitating agent to the composition to provide a mixture comprising a precipitate, wherein the precipitate comprises the peptide intermediate, wherein the precipitating agent comprises an alcohol having three or more carbon atoms, and where the precipitating agent is present in an amount of at least 5 volumes of precipitating agent to total peptide composition volume prior to addition of the precipitating agent; and (c) collecting the precipitate.

In still further aspects, the invention provides a method of filtering a peptide precipitate comprising steps of: (a) determining information indicative of filterability of a peptide precipitate as a function of a relative amount of a precipitating agent used to cause precipitation; and (b) using the information obtained in step (a) to filter a peptide precipitate.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The invention provides methods for recovery of peptide material synthesized by any standard methodology. To facilitate the discussion of the invention, use of the invention to recover a particular 16-residue peptide intermediate (SEQ ID NO: 3) during synthesis of a peptide product will be discussed. However, it is understood that the methods disclosed are applicable to any peptide recovery needs, and are not limited to the particular peptide intermediate exemplified herein.

The present invention is directed to methods for effectively synthesizing peptides and peptide intermediates, and in particular for isolating peptide material from solution. Such methods in accordance with preferred embodiments of the present invention can advantageously be used to provide improved commercial scale processes for synthesis and recovery of peptide materials.

The methods described herein are particularly suitable for improving aspects of scaled-up synthesis of peptides. In preferred embodiments, the inventive methods can provide such improvements as reduction in processing (synthesis) time, improvements in the yield of products, improvements in product purity, and reduction in amount of reagents and starting materials required.

The processes of the present invention can be used in connection with the synthesis of peptides of any suitable length and/or sequence. It will be understood that the peptides of the invention can be synthesized or prepared by techniques well known in the art. See, for example, Creighton, 1983, Proteins: Structures and Molecular Principles, W.H. Freeman and Co., NY, as well as additional references cited herein.

In some aspects, the invention can be utilized to recover peptides that incorporate about 2 to about 500, or about 4 to about 100, or about 5 to about 50 residues of one or more amino acids. Residues of one or more other monomeric, oligomeric, and/or polymeric constituents optionally can be incorporated into a peptide. Non-peptide bonds may also be present. These non-peptide bonds can be between amino acid residues, between an amino acid and a non-amino acid residue, or between two non-amino acid residues. These alternative non-peptide bonds can be formed by utilizing reactions well known to those in the art, and may include, but are not limited to, imino, ester, hydrazide, semicarbazide, azo bonds, and the like.

As used herein, the term "monomer" means a relatively low molecular weight material (i.e., generally having a molecular weight less than about 500 Daltons) having one or more polymerizable groups. "Oligomer" means a relatively intermediate sized molecule incorporating two or more monomers and generally having a molecular weight of from about 500 up to about 10,000 Daltons. "Polymer" means a relatively large material comprising a substructure formed two or more monomeric, oligomeric, and/or polymeric constituents and generally having a molecular weight greater than about 10,000 Daltons.

The amino acids from which the peptides are derived can be naturally occurring amino acid residues, non-natural amino acid residues, or combinations thereof. The twenty common naturally-occurring amino acid residues are as follows: A (Ala, alanine), R (Arg, arginine); N (Asn, asparagine); D (Asp, aspartic acid); C (Cys, cysteine) Q (Gln, glutamine), E (Glu, glutamic acid); G (Gly, glycine); H (His, histidine); I (Ile, isoleucine); L (Leu, leucine); K (Lys, lysine); M (Met, methionine); F (Phe, phenylalanine); P (Pro, proline); S (Ser, serine); T (Thr, threonine); W (Trp, tryptophan); Y (Tyr, tyrosine); and V (Val, valine). Naturally occurring rare amino acids are also contemplated and include, for example, selenocysteine and pyrrolysine.

Non-natural amino acids include organic compounds having a similar structure and reactivity to that of naturally-occurring amino acids and include, for example, D-amino acids, beta amino acids, omega-amino acids (such as 3-aminopropionic acid, 2,3-diaminopropionic acid, 4-aminobutyric acid, and the like), gamma amino acids, cyclic amino acid analogs, propargylglycine derivatives, 2-amino-4-cyanobutyric acid derivatives, Weinreb amides of α-amino acids, and amino alcohols.

The present invention contemplates that the recovered peptide material may act as intermediates in the synthesis of other peptides of interest through modification of the resultant peptide, through coupling of the peptide to other materials such as other peptides, or the like. For example, the present invention would be particularly useful to recover peptide fragment intermediates useful in the synthesis of enfuvirtide (also known as the T-20 peptide), or alternatively DP-178. Such peptide fragments of the invention include, but are not limited to, those having amino acid sequences as depicted in Table 1 below:

TABLE 1

| PEPTIDE NO. | AMINO ACID SEQUENCE | SEQ ID NO | CORRESPONDING AMINO ACID SEQUENCE OF T-20 |
|---|---|---|---|
| 1 | YTSLIHSL | (SEQ ID NO: 2) | 1-8 |
| 2 | YTSLIHSLIEESQNQ | (SEQ ID NO: 3) | 1-15 |
| 3 | YTSLIHSLIEESQNQQ | (SEQ ID NO: 4) | 1-16 |
| 4 | YTSLIHSLIEESQNQQEK | (SEQ ID NO: 5) | 1-18 |
| 5 | IEESQNQ | (SEQ ID NO: 6) | 9-15 |
| 6 | IEESQNQQ | (SEQ ID NO: 7) | 9-16 |
| 7 | QEKNEQELLELDKWASLWNW | (SEQ ID NO: 8) | 16-35 |
| 8 | QEKNEQELLELDKWASLWNWF | (SEQ ID NO: 9) | 16-36 |
| 9 | EKNEQEL | (SEQ ID NO: 10) | 17-23 |
| 10 | EKNEQELLEL | (SEQ ID NO: 11) | 17-26 |
| 11 | EKNEQELLELDKWASLWNWF | (SEQ ID NO: 12) | 17-36 |
| 12 | NEQELLELDKWASLWNW | (SEQ ID NO: 13) | 19-35 |
| 13 | NEQELLELDKWASLWNWF | (SEQ ID NO: 14) | 19-36 |
| 14 | LELDKWASLWNW | (SEQ ID NO: 15) | 24-35 |
| 15 | LELDKWASLWNWF | (SEQ ID NO: 16) | 24-36 |
| 16 | DKWASLWNW | (SEQ ID NO: 17) | 27-35 |
| 17 | DKWASLWNWF | (SEQ ID NO: 18) | 27-36 |
| 18 | EKNEQELLELDKWASLWNW | (SEQ ID NO: 19) | 17-35 |

Enfuvirtide is a peptide that corresponds to amino acid residues 638 to 673 of the transmembrane protein gp41 from HIV-1.sub.LAI isolate and has the 36 amino acid sequence (reading from amino, $NH_2$ to carboxy, COOH, terminus):

$NH_2$—YTSLIHSLIEESQNQQEKNEQELLELDK-WASLWNWF-COOH (SEQ ID NO:1)

The chemical name of enfuvirtide is N-acetyl-Tyr-Thr-Ser-Leu-Ile-His-Ser-Leu-Ile-Glu-Glu-Ser-Gln-Asn-Gln-Gln-Glu-Lys-Asn-Glu-Gln-Glu-Leu-Leu-Glu-Leu-Asp-Lys-Trp-Ala-Ser-Leu-Trp-Asn-Trp-Phe-$CONH_2$ (SEQ ID NO:1). It will be understood that the principles of the present invention may also be applied in preferred embodiments to the recovery of peptides constituting all or a portion of T-20-like peptide fragments in addition to T-20 peptide fragments. The term "T-20-like" as used herein includes any HIV or non-HIV peptide listed in U.S. Pat. Nos. 5,464,933; 5,656,480, 6,015,881, 6,281,331, and/or PCT Publication No. WO 96/19495. The synthesis of peptides having T-20 activity and peptide intermediates used to prepare peptides having T-20 activity are described in U.S. Pat. Nos. 5,464,933; 5,656,480 and PCT Publication No. WO 96/19495.

In addition to peptides useful in the synthesis of enfuvirtide and enfuvirtide-like peptides, the principles of the present invention may be advantageously used to recover the following peptide material, fragment intermediates thereof, and/or analogs from a support after solid phase synthesis: oxytocin; vasopressin analogues such as Felypressin, Pitressin, Lypressin, Desmopressin, Perlipression; Atosiban; adrenocorticotropic hormone (ACTH); Insulin, Glucagon; Secretin; calcitonins: human calcitonin, salmon calcitonin, eel calcitonin, dicarba-eel (elcatonin); luteinizing hormone-releasing hormone (LH-RH) and analogues: leuprolide, deslorelin, triptorelin, goserelin, buserelin; nafarelin, cetrorelix, ganirelix, parathyroid hormone (PTH); human corticotrophin-releasing factor, ovine corticotrophin-releasing factor; growth hormone releasing factor; somatostatin; lanreotide, octretide, thyrotripin releasing hormone (TRH); thymosin-1; thomopentin (TP-5); cyclosporin; integrilin; angiotensin-converting enzyme inhibitors: enalapril, lisinopril.

The invention contemplates recovery of peptide material that has been chemically altered to contain one or more chemical groups other than amino acid residues, sometimes referred to as modified peptides. Such chemical groups can be included at the amino termini of the peptides, the carboxy termini, and/or at one or more amino acid residues along the length of the peptide. In still further embodiments, the peptide can include additional chemical groups present at their amino and/or carboxy termini, such that, for example, the stability, reactivity and/or solubility of the peptides are enhanced. For example, hydrophobic groups such as dansyl, acetyl, t-butyloxycarbonyl, or 9-fluorenylmethoxy-carbonyl groups can be added to the amino termini of peptides. Additionally, the hydrophobic group, t-butyl, or an amido group can be added to the carboxy termini of peptides. Similarly, a para-nitrobenzyl ester group can be placed at the carboxy termini of peptides. Techniques for introducing such modifications are well known in the art.

In some aspects, the invention can be utilized to recover peptide material that can optionally include protecting groups. For example, the invention can be used to recover peptide intermediates. According to these embodiments, the peptide intermediates include at least one side chain protecting group. The peptide intermediates can be fully protected, such that all side chain reactive groups include protecting groups, and the appropriate terminal amino acids include protecting groups. In other aspects, the invention can be utilized to recover peptides that do not include any protecting groups (such peptides can be referred to as globally deprotected peptides when all protecting groups have been removed by a reagent).

The nature and use of protecting groups is well known in the art. Generally, a suitable protecting group is any sort of group that can help prevent the atom to which it is attached, typically oxygen or nitrogen, from participating in undesired reactions during processing and synthesis. Protecting groups include side chain protecting groups and amino- or N-terminal protecting groups. Protecting groups can also prevent reaction or bonding of carboxylic acids, thiols, and the like.

A side chain protecting group refers to a chemical moiety coupled to the side chain (R group in the general amino acid formula $H_2N—C(R)(H)—COOH$) of an amino acid that helps prevent a portion of the side chain from reacting with chemicals used in steps of peptide synthesis, processing, and the like. The choice of a side chain protecting group can depend upon various factors, for example, the type of synthesis performed, processing to which the peptide will be subjected, and the desired intermediate product or final product. The side chain protecting group also depends upon the nature of the amino acid itself. Generally, a side chain protecting group is chosen that is not removed during deprotection of the α-amino groups during synthesis. Therefore, the α-amino protecting group and the side chain protecting group are typically not the same.

In some cases, and depending upon the type of reagents used in solid phase synthesis and other peptide processing, an amino acid may not require the presence of a side chain protecting group. Such amino acids typically do not include a reactive oxygen or nitrogen in the side chain.

Examples of side chain protecting groups include acetyl (Ac), benzoyl (Bz), tert butyl, triphenylmethyl (trityl), tetrahydropyranyl, benzyl ether (Bzl), 2,6-dichlorobenzyl (DCB), t-butoxycarbonyl (BOC), nitro, p-toluenesulfonyl (Tos), adamantyloxycarbonyl, xanthyl (Xan), benzyl, methyl, ethyl, and t-butyl ester, benzyloxycarbonyl (Z), 2-chlorobenzyloxycarbonyl (2-Cl-Z), t-amyloxycarbonyl (Aoc), and aromatic or aliphatic urethan-type protecting groups, photolabile groups such as nitro veratryl oxycarbonyl (NVOC), and fluoride labile groups such as trimethylsilylethyl oxycarbonyl (TEOC).

For example, any one or more of the side chains of the amino acid residues of peptide fragments listed in Table 1 can be protected with standard protecting groups such as t-butyl (t-Bu), trityl (trt), and t-butyloxycarbonyl (Boc). Preferred side chain protecting groups include the t-Bu group for tyrosine, threonine, serine and aspartic acid amino acid residues; the trt group for histidine, glutamine, and asparagine amino acid residues; and the Boc group for lysine and tryptophan amino acid residues.

During the synthesis of fragments of Table 1 that include histidine, the side chain of the histidine residue desirably is protected, preferably with a trityl (trt) protecting group. If the histidine residue is not protected, reagents utilized in synthesis and processing of peptides (for example, the acid used to cleave the peptide fragment from the resin in solid phase synthesis) could detrimentally react with the histidine residue, causing unintended elaboration of the peptide fragment.

Preferably, the glutamine residues of the peptide fragments of the invention are protected with trityl (trt) groups. However, it is preferred not to protect the glutamine residue at the carboxy-terminal end of fragments 1-16 and 9-16. It has been found that the absence of a protective group on the glutamine residue at the carboxy-terminal end of the 1-16 fragment facilitates reaction of the 1-16 fragment with the 17-36 fragment, allowing coupling of the fragments with only about 2% racemization. In addition, if lower solubility of any of the peptide fragments of the invention in organic solvents is desired, the trityl protecting groups may be eliminated from any one or more of the other glutamine residues of the fragments.

Preferably, all the asparagine residues of each peptide fragment of the invention are protected. In addition, it is preferred that the tryptophan residue is protected with a Boc group.

An amino terminal protecting group includes a chemical moiety coupled to the alpha amino group of an amino acid. Typically, the amino-terminal protecting group is removed in a deprotection reaction prior to the addition of the next amino acid to be added to the growing peptide chain, but can be maintained when the peptide is cleaved from the support. The choice of an amino terminal protecting group can depend upon various factors, for example, the type of synthesis performed and the desired intermediate product or final product obtained.

Examples of amino terminal protecting groups include: (1) acyl-type protecting groups, such as formyl, acryloyl (Acr), benzoyl (Bz) and acetyl (Ac); (2) aromatic urethan-type protecting groups, such as benzyloxycarbonyl (Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as 9-fluorenylmethyloxycarbonyl (Fmoc), cyclopentyloxycarbonyl, adamantyloxycarbonyl, and cyclohexyloxycarbonyl; and (5) thiourethan-type protecting groups, such as phenylthiocarbonyl. Preferred protecting groups include 9-fluorenylmethyloxycarbonyl (Fmoc), 2-(4-biphenylyl)-propyl(2)oxycarbonyl (Bpoc), 2-phyenlpropyl (2)-oxycarbonyl (Poc), and t-butyloxycarbonyl (Boc).

Representative process embodiments, wherein peptides are made using SPPS techniques, will now be described in more detail. Any type of support suitable in the practice of SPPS can be used in accordance with the inventive methods. In preferred embodiments, the support comprises a resin that can be made from one or more polymers, copolymers, or combinations of polymers such as polyamide, polysulfamide, substituted polyethylenes, polyethylene glycol, phenolic resins, polysaccharides, or polystyrene. The polymer support can also be any solid that is sufficiently insoluble and inert to solvents used in peptide synthesis. The solid support typically includes a linking moiety to which the growing peptide is coupled during synthesis and which can be cleaved under desired conditions to release the peptide from the support. Suitable solid supports can include linkers that are photo-cleavable, TFA-cleavable, HF-cleavable, fluoride ion-cleavable, reductively-cleavable, Pd(O)-cleavable, nucleophilically-cleavable, or radically-cleavable. Preferred linking moieties are cleavable under conditions such that the cleaved peptide is still substantially protected by side chain protecting groups.

Preferred solid supports include acid sensitive solid supports, for example, hydroxymethyl-polystyrene-divinylbenzene polymer resin ("Wang" resins, see Wang, S. S. 1973, J. Am. Chem. Soc., 95:1328-33), 2-chlorotrityl chloride resin (see Barlos et al. (1989) Tetrahedron Letters 30(30):3943-3946), and 4-hydroxymethyl-3-methoxyphenoxybutyric acid resin (see Richter et al. (1994), Tetrahedron Letters 35(27): 4705-4706), as well as functionalized, crosslinked poly N-acryloylpyrrolidone resins, and chloromethylpolystyrene dinvinylbenzene polymer resins. These types of solid supports are commercially available from, for example, Calbiochem-Novabiochem Corp., San Diego, Calif.

When SPPS is utilized, the synthesized peptide is preferably cleaved from the solid support (such as a resin) prior to utilization of the inventive methods described herein. Peptides synthesized via SPPS techniques can be cleaved using techniques well known to those skilled in the art. For example, solutions of 1% or 2% trifluoracetic acid (TFA) in DCM or a combination of a 1% and a 2% solution of TFA in DCM can be used to cleave the peptide. Alternatively, acetic acid (HOAC) can be used to cleave the peptide. The specific cleavage reagent, solvents and time selected for cleavage will depend upon the particular peptide being cleaved. These parameters are within the skill in the relevant art.

General procedures for production and loading of resins that can be utilized in SPPS are described in "Principles and Practice of Solid Phase Peptide Synthesis" (Edited by Greagory A. Grant, 1992, W.H. Freeman and Company) and references therein, and are well known to those of ordinary skill in the art. Specific procedures for loading of Wang resins are described for example in Sieber (1987) Tet. Lett. 28:6147-50, and Granadas et al. (1989), Int. J. Pept. Protein Res. 33:386-90.

As noted herein, Fmoc is a protecting group used in certain embodiments for protection of the α-amino moiety of an amino acid. Depending upon which amino acid is being loaded, and at what point in the peptide fragment intermediate it is to be attached, the side chain of the amino acid may or may not be protected.

In some embodiments, the peptide fragment intermediates of the invention are synthesized by SSPS techniques using standard Fmoc protocols. See, for example, Carpin et al. (1970), J. Am. Chem. Soc. 92(19):5748-5749; Carpin et al. (1972), J. Org. Chem. 37(22): 3404-3409, "Fmoc Solid Phase Peptide Synthesis," Weng C. Chan and Peter D. White Eds. (2000) Oxford University Press Oxford Eng. The Fmoc-protected amino acids, either with or without side-chain protecting groups as desired, that are used in loading the resin and in peptide synthesis are available commercially from Genzyme Pharmaceuticals Inc., Cambridge, Mass.; Bachem Biosciences Inc., Torrance, Calif.; Senn Chemicals, Dielsdorf, Switzerland; and Orpegen Pharma, Heidelberg, Germany, or are readily synthesized using materials and methods well known in the art. As an alternative to the above procedure, the resin can be purchased, for example, pre-loaded with the appropriate Fmoc-α-N-protected amino acid (for example, from Bachem Biosciences Inc. or Senn Chemicals).

The loaded resin is washed with a solvent, such as NMP. The resin is then agitated with nitrogen bubbling in a swelling solvent to swell the resin beads. The Fmoc group is removed from the terminal amine using piperidine in NMP. The deprotected resin is then washed with NMP to remove Fmoc by-products and residual piperidine.

The amino acid residue or fragment to be coupled is activated for reaction at its carboxy terminus and coupled. The coupling cycle is repeated for each of the subsequent amino acid residues of the peptide fragment intermediate. Following the final coupling cycle, the resin is washed with a solvent such as NMP, and then washed with an inert second solvent such as DCM. Peptide fragment intermediates synthesized via SPPS techniques can be cleaved from the resin using techniques well known to those of skill in the art, for example by the addition of a solution of an acid such as TFA in DCM. The cleaved peptide intermediate can then be isolated.

The methods of the invention, which are directed to precipitating peptides, can be integrated into any peptide synthesis procedure, such as solid phase, liquid phase, hybrid synthesis, or recombinant synthesis. The methods of the invention comprise addition of a precipitating agent to a peptide composition to precipitate the peptide from the composition. The peptide composition includes peptide and one or more inert solvents, such as dichloromethane (DCM), dimethylformamide (DMF), dimethylsulfoxide (DMSO), dichloroethane (DCE), dimethyl acetamide, and/or other common solvents utilized in peptide synthesis. In other embodiments, the invention provides methods of controlling the relative amount of precipitating agent added to impact the purity of the precipitated peptide. In still further embodiments, the invention provides methods for selecting precipitating agents based upon the impact the precipitating agent will have on impurities in the precipitate.

In one aspect of this embodiment, the concentration of peptide in the solvent, prior to addition of the precipitating agent is at least about 2 mg/ml, or at least about 4, or at least about 10 mg/ml, or at least about 15 mg/ml, or at least about 20 mg/ml.

In certain aspects of the invention, the mixing energy applied during synthesis can impact the processability of the peptide precipitate. Mixing energy is provided to the peptide recovery system by such mechanisms as agitation or stirring, for example. If the mixing energy provided is too slow, the peptide precipitate can comprise large, tacky agglomerates of peptide material that can be difficult, if not impossible to process. On the other hand, if the mixing energy provided is too fast, the system can generate fines which can in turn clog the processing equipment, such as filtration devices. Accordingly, the mixing energy is chosen to provide suitable mixing of the precipitating agent with the peptide composition to in turn provide a processable peptide precipitate. The mixing energy can be adjusted to achieve the desired processability.

As mentioned herein, the invention provides methods of precipitating peptides from a peptide composition. The peptides to be recovered from the composition can be in the form of peptide intermediates (thus including at least one side chain protecting group), or peptides that do not include any protecting groups.

Generally, the presence of side chain protecting groups (particularly those protecting groups that include methyl groups) can render the peptide intermediate more soluble in nonpolar solvents, such as DCM. In some aspects, the invention provides methods for recovery of peptide intermediates without requiring a deprotection step, where protecting groups would be removed from the peptide intermediate before isolation of the peptide. Thus, in preferred embodiments of the invention, the methods can allow elimination of deprotection steps and the reagents involved in these steps during synthesis of peptides.

In preferred embodiments, the precipitating agent comprises an alcohol that includes three or more carbon atoms, and at least one hydroxyl group. Preferably, the alcohol is a secondary or tertiary alcohol, such that that hydroxyl group is more sterically hindered than a primary hydroxyl group. Preferably, the precipitating agent is relatively inert with respect to the peptide to be precipitated, such that the precipitating agent does not chemically react with the peptide and/or other moieties present in the composition (for example, to form the ethyl ester of the peptide to be isolated). One particularly preferred precipitating agent is isopropyl alcohol.

The precipitating agent is provided to the peptide composition in an amount sufficient to precipitate the peptide material from solution. Preferably, the amount of precipitating agent is chosen to provide improved purity of the peptide precipitate. In some embodiments, the precipitating agent is provided in an amount of at least about 5 volumes or in the range of 5 to 8 volumes per volume of peptide solution. In alternative embodiments, the precipitating agent is provided in an amount in the range of 6.5 to 7.5 volumes per volume of peptide solution.

As illustrated in the Examples, addition of IPA to the peptide solution can cause precipitation of the peptide from solution wherein the precipitated peptide has a higher purity than that obtained utilizing standard precipitating compositions, such as heptane. For example, utilization of IPA as the precipitating agent can provide a peptide precipitate with 50% less impurities as compared to peptide precipitated with heptane. While not intending to be bound by a particular theory, it is believed that heptane is a non-polar solvent and thus precipitates all material. In contrast, IPA has a suitable degree of polarity to cause precipitation of peptide while retaining impurities (such as, for example, truncated species) in solution.

The invention is further directed to methods for concentrating peptide material from solution, which comprises collecting precipitated peptide material. In some embodiments, peptide precipitates are generated by adding at least one precipitating agent to a composition comprising the peptide material of interest, and collecting the precipitated material comprising the peptide material of interest. In some embodiments, the method comprises the steps of providing a composition comprising a peptide material in a solvent comprising DCM; precipitating the peptide material by adding a precipitating agent to the composition to provide a mixture comprising a precipitate, wherein the precipitate comprises the peptide material, and wherein the precipitating agent is an alcohol with three or more carbon atoms.

If desired, the resulting precipitated peptide can be redissolved and subjected to additional precipitation. For example, the precipitated peptide can be redissolved in a suitable peptide solvent, additional precipitating agent added to the solution, and peptide precipitate collected as described herein. Such successive precipitation steps can be repeated as desired.

Precipitated peptide material can be collected by various methods well known in the art including, for example, filtration and centrifugation. In some embodiments, the precipitated peptide is collected by vacuum filtration through polypropylene filter cloth. The precipitated peptide can optionally be washed, if desired, utilizing common reagents.

In one such embodiment, the invention provides methods of impacting the filterability of a peptide precipitate by determining the amount of IPA relative to the total solution volume prior to addition of the IPA, and using the determined amount to impact the filterability of the peptide when precipitated from the composition. In another embodiment, the methods can further involve obtaining information relating to mixing energy during precipitation, and using the mixing energy information and the amount of precipitating agent relative to the total solution volume prior to addition of the precipitating agent to impact filterability of the peptide when precipitated from the composition. Accordingly, the filtration rate can be controlled by utilization of composition content and agitation rate during the isolation process, thereby providing adjustability to the isolation process as a whole.

In some embodiments, the mixing energy is applied in the form of agitation at a rate in the range of less than about 2.5 m/s, or in the range of about 0.25 to about 2.5 m/s, or in the range of about 0.4 to about 2 m/s, or in the range of about 1 to about 2 m/s.

The invention will now be described with reference to the following non-limiting examples.

EXAMPLES

For the following examples, the following standard reagents and nomenclature are adopted:

Standard Filtration Equipment: 35-mm Millipore filter with a 5µ nylon filter medium, under 100 mm Hg vacuum.

Chloranil test: The chloranil test solution was prepared by adding a drop of a saturated solution of chloranil in toluene to about 1 ml of acetone. The NMP washings were tested by adding a drop of the washing to the chloranil test solution. A blue or violet color is a positive indication for the presence of secondary amine, indicating that Fmoc by-products and/or residual piperidine are still present.

Ninhydrin test: In the qualitative ninhydrin test, a 2-20 mg sample of the resin was withdrawn and washed with NMP and subsequently DCM or methanol. Three drops of a 76% solution of phenol in ethanol, six drops of a 0.2 mM KCN solution in pyridine, and three drops of a 0.28 M solution of ninhydrin in ethanol were added to the sample, and the sample was placed in a heating block at about 70-80° C. for about 5 minutes. The sample was removed and immediately diluted with an ethanol/water solution (9:1). A blue or violet color in the supernatant solution or beads is a positive indication of the presence of free amines, including that the reaction is not yet complete. If a positive ninhydrin test was observed after one hour of coupling reaction, the coupling reaction was continued for an additional hour. If a positive ninhydrin test occurred after 3 hours of coupling reaction, the vessel was drained, and the coupling was repeated using about one equivalent of activated amino acid and reagents.

Fragment-1: The peptide intermediate denoted Fragment-1 was synthesized utilizing an air-sensitive 2-chlorotritylchloride resin, utilizing standard solid phase peptide synthesis techniques. In the Examples, Fragrnent-1 has the following properties:

Sequence: Ac-Tyr(tBu)-Thr(tBu)-Ser(tBu)-Leu-Ile-His(trt)-Ser(tBu)-Leu-Ile-Glu(tBu)-Glu(tBu)-Ser(tBu)-Gln(trt)-Asn(trt)-Gln(trt)-Gln-OH (SEQ ID NO: 3).

Formula: $C_{186}H_{237}N_{22}O_{31}$

MW: 3274.76.

Example 1

Isolation of Peptide Intermediate with IPA

This example demonstrates the successful isolation of a 16-residue peptide, present initially as an emulsion in DCM, utilizing isopropyl alcohol.

The initial peptide material was present as an emulsion of Fragment-1 in DCM. In order to prepare the emulsion for peptide precipitation, the emulsion was treated by adding DCM and vacuum stripping (VD-800-243 vacuum stripper).

The resulting clear DCM solution was drummed off, weighed (228.2 kg) and sampled. Analysis of the sample obtained from the 228.2 kg in the drum was found to contain 4.23% (w/w) Fragment-1 (81.0% area norm, AN). The sample was assayed by external standard HPLC analysis.

Analysis indicated a contained Fragment-1 amount of 9.65 kg. The "actual" Fragment-1 content was then estimated by dividing the measured contained Fragment-1 by the area normalized percent. Utilizing this calculation, the actual Fragment-1 content was determined to be 13.5 kg.

The solution was then charged back into the vacuum, and concentrated to 45 L prior to isolation.

After concentration, IPA was added to the Fragment-1 solution in an amount of 260 kg. The solution was then reduced by vacuum distillation under gentle agitation to provide an IPA to DCM solution volumetric ratio of 7.3. The agitator tip speed during distillation was 1.6 m/s. After distillation, the final vessel volume was 180 L. Total distillation time was 12 hours, and the distillation rate was 16.2 L/hr.

The solution was aged for 4 hours, with an agitator tip speed during age of 1.6 m/s.

After distillation, the vessel was then cooled to 20° C. and the resulting slurry isolated in a Nutsche filter fitted with a polypropylene filter cloth (pore size 10μ, filtration area 0.256 m$^2$). Filtration was performed for 1 hour at a pressure of 8 psig. Jacket temperature during filtration was maintained at 35-37° C., and the vacuum range was maintained at 525-100 mm Hg.

The filtrate was washed with 79.3 kg IPA for 3 hours and 18 minutes. After washing, the effluent volume was 230 L, with 0.95 kg Fragment-1 in the effluent.

The filtration product was then dried for 36 hours in a double cone dryer (PP-DV-111) with a jacket temperature of 35-37° C. Vacuum range was maintained at 30-15 mm Hg. Final loss of solvent/water on drying (LOD) was 0.01. 9.2 kg of product was obtained.

Analytical Results

The isolated Fragment-1 obtained was then analyzed by HPLC. In addition to determining the area normalized percent, the method was also used to determine the wt/wt % assay by the external standard technique.

Results are summarized in Table 2 below. As shown in Table 2, utilization of IPA to isolate the peptide intermediate provided a reduction in impurities of approximately 50% in the isolated peptide, as compared to heptane (94% versus 88% AN).

Example 2

Isolation of Peptide Intermediate with IPA

This example demonstrates the successful isolation of a 16-residue peptide, present initially a homogeneous solution of Fragment-1 in DCM, utilizing isopropyl alcohol.

In this Example, the distillation was performed at a higher agitation rate than in Example 1, in an attempt to obtain better heat transfer. However, this higher agitation rate generated fines that blinded the filter cloth and stopped the filtration. Thus, the batch was re-dissolved in DCM and reprecipitated. The isolation procedure was then restarted with the re-dissolved DCM solution.

The initial peptide material was a homogeneous solution of Fragment-1 in DCM weighing 65.5 kg. Analysis indicated it contained a 20.6% (wt/wt) Fragment-1 (79.6% AN), for a contained Fragment-1 amount of 13.5 kg. The estimated equivalent "actual" yield was determined to be 17.0 kg. The DCM solution was treated by adding DCM and vacuum stripping (VD-800-243) to give a solution that weighed 65.6 kg. The solution was concentrated to 45 L of solution.

IPA was added to the solution in an amount of 284.2 kg, to give an IPA to DCM solution volumetric ratio of 6.9. The solution was then reduced to target volume by vacuum distillation. The agitator tip speed was 2.6 m/s, vacuum range 130-39 mm Hg for distillation. Distillation was performed at a rate of 18.8 L/hr for 12 hours. Final vessel volume was 185 L. Fines generated during distillation blinded the filter cloth and stopped the filtration.

The solution was aged for 4 hours, and agitator tip speed during age was 2 ml/s.

The slurry in the filter was then transferred back to the distillation vessel along with the mother liquors. DCM in an amount of 99 kg was added to the batch to re-dissolve the solids, giving 118 kg solution. The contained Fragment-1 was determined to be 13.5 kg, with the calculated "actual" Fragment-1 of 17.0 kg.

IPA was added in an amount of 381 kg, giving an IPA to DCM solution volumetric ratio of 5.3. The batch was then stripped a second time, but with the same agitator speed as in Example 1 (1.6 m/s). For this (second) distillation, the vacuum range was maintained at 200-20 mm Hg, and jacket temperature was 38° C. Distillation was performed at a rate of 28 L/hr for 14 hours. Final vessel volume was 185 L.

The solution was aged for 2 hours, and agitator tip speed during age was 1.6 m/s. The Fragment-1 IPA slurry was then isolated in a Nutsche filter fitted with a polypropylene filter cloth (pore size 10μ, filtration area 0.256 m$^2$). The slurry generated solid agglomerates without any fines. Filtration was performed at a pressure of 0 psig for 2 hours and fifteen minutes (main body filtration). During filtration, vacuum was maintained at 400-100 mm Hg.

The filtrate was washed with 86.7 g IPA for 7 hours. Blow down time was 6 hours. Filtrate thickness was 7 inches. The effluent volume was 240 L, and 1.37 kg of product was present in the effluent.

The filtrate was dried for 74 hours in a double cone dryer (PP-DV-111) with a jacket temperature of 38° C. Vacuum range was 16-7 mm Hg. Final LOD was 0.86. 14.0 kg product was obtained.

Analytical Results

The isolated Fragment-1 obtained was then analyzed by HPLC. In addition to determining the area normalized percent, the method was also used to determine the wt/wt % assay by the external standard technique.

Results are summarized in Table 2 below. As shown in Table 2, utilization of IPA to isolate the peptide intermediate provided a reduction in impurities of approximately 50% in the isolated peptide, as compared to heptane. The AN and w/w % of Fragment-1 in the precipitate were comparable to that obtained in Example 1.

Example 3

Comparison to Heptane Process

This example compares the isolation of Fragment-1 utilizing heptane with the inventive methods.

A 130 ml slurry containing Fragment-1 in heptane was obtained. The slurry contained large solid particles, as observed via microscopy, and settled very rapidly. The sample was filtered in the laboratory in 3 minutes 14 seconds. Filtrations were performed using a 35 mm Millipore filter with a 5μ nylon filter medium. Filtration was done under 100 mg Hg vacuum.

A comparison of isolated peptide material using IPA versus heptane is shown in Table 3 below.

HPLC analysis of Fragment-1 obtained utilizing heptane versus IPA (data not shown) indicated that utilizing IPA removes approximately 50% of impurities. As shown in Table 3, precipitation with IPA yielded product with purity of 94%, versus the 88% purity obtained using heptane. This reduction from 12% impurities to 6% impurities in the precipitated Fragment-1 represented a 50% reduction in impurities in the product. Further, as illustrated in Table 3, precipitation with IPA required only one distillation step, compared to the four distillation steps required when heptane was utilized for precipitation of the peptide fragment.

TABLE 2

Purity of Recovered Fragment-1.

|  | Heptane | IPA (Example 1) | IPA (Example 2) |
|---|---|---|---|
| T1327 AN | 88.1% | 94.1% | 94.3% |
| T1327 w/w | 77.0% | 87.0% | 86.4% |
| Cont/cont | N/C | 82.5% | 89.6% |
| Act/Act | N/C | 73.0% | 80.9% |

* N/C: not calculated.

TABLE 3

Comparison of IPA to Heptane as Precipitating agent.

|  | Heptane | IPA |
|---|---|---|
| Solvent boiling point | 98° C. | 82.5° C. |
| Distillation | 4 shots | Once |
| Lab filtration time (min:sec) | 3:14 | 4:19 |
| Purity | 88% | 94% |

Example 4

Isolation of Peptide Intermediate with IPA

This Example demonstrates isolation of a peptide intermediate from DCM solution utilizing IPA.

The initial peptide material was present as a 58.4 kg solution of Fragment-1 in DCM. The solution contained 17.3% (w/w) Fragment-1, and the solution density was 1.29. The sample was assayed by external standard HPLC analysis. Analysis indicated a contained Fragment-1 amount of 10.1 kg. The "actual" Fragment-1 content was determined to be 13.2 kg.

IPA was then added to the solution in an amount of 360 ml, to give an IPA to DCM solution volumetric ratio of 8.0. The solution was then reduced to target volume by vacuum distillation. The solution was not agitated during distillation, and the vacuum range was 100-50 mm Hg. Jacket temperature was 25° C. Final vessel volume was 325 L.

The solution was aged for 12 hours. The Fragment-1 PA slurry was then isolated in a Nutsche filter fitted with a polypropylene filter cloth (pore size 10 μl, filtration area 0.256 m²). Filtration was performed at a temperature of 0° C.

The filtrate was dried in a double cone dryer (PP-DV-111) with a jacket temperature of 38° C. Vacuum range was 16-7 mm Hg. Final LOD was 0.86. Drying time was 74 hours, and 14.0 kg of product was obtained.

Analytical Results

The isolated Fragment-1 obtained was analyzed by HPLC. In addition to determining the area normalized percent, the method was also used to determine the wt/wt % assay by the external standard technique. Results are summarized in Table 4. Also listed in Table 4 are the results obtained for the batches that were the source of the starting DCM concentration used in this Example. Results indicated that using IPA in place of heptane to isolate peptide intermediate Fragment-1 removes approximately 50% of the impurities (94% versus 87% AN).

Example 5

Isolation of Fragment-1 Using IPA

This Example demonstrates isolation of peptide from DCM solution utilizing IPA.

The initial peptide material was present as a 70 ml solution of Fragment-1 in DCM. The solution contained 13.3% (w/w) Fragment-1, and the solution density was 1.29. The sample was assayed by external standard HPLC analysis. Analysis indicated a contained Fragment-1 amount of 12 g. The "actual" Fragment-1 content was determined to be 15.3 g.

IPA was then added to the solution in an amount of 460 ml, to give an IPA to DCM solution volumetric ratio of 6.6. The solution was then reduced to target volume by vacuum distillation. Distillation was performed for 6 hours, 27 minutes at a rate of 44.6 L/hour. The agitator tip speed during distillation was 0.4 m/s, and the vacuum range was 100-50 mm Hg. Jacket temperature was 25-3° C. Final vessel volume was 240 L.

The Fragment-1 PA slurry was then isolated in a Nutsche filter fitted with a polypropylene filter cloth (pore size 10μ, filtration area 0.256 m²). Filtration was performed at a temperature of 20° C., and filtration time was 4 minutes, 15 seconds (main body filtration).

The filtrate was dried in a double cone dryer (PP-DV-111) with a jacket temperature of 38° C. Vacuum range was 16-7 mm Hg. Final LOD was 0.86. Drying time was 74 hours, and 14.0 kg of product was obtained.

Analytical Results

The isolated Fragment-1 obtained was analyzed by HPLC. In addition to determining the area normalized percent, the method was also used to determine the wt/wt % assay by the external standard technique. Results are summarized in Table 4. Also listed in Table 4 are the results obtained for the batches that were the source of the starting DCM concentration used in this Example. Results indicate that using IPA in place of heptane to isolate peptide intermediate Fragment-1 removes approximately 50% of the impurities (94% versus 88% AN).

TABLE 4

Recovery of Peptide Intermediate Using IPA:

|  | Batch #1 | | Batch #2 | |
|---|---|---|---|---|
|  | DCM/Heptane slurry* | IPA (Example 4) | DCM/IPA* | IPA (Example 5) |
| T1327V AN | 87.8% | 93.7% | 86.2% | 94.1% |
| W/w | 76.4% | 88.8% | 71.7% | 88.8% |
| Cont/cont | N/a | 85.0% | N/a | 82.2% |
| Act/act | 100% assumed | 73.3% | 100% assumed | 73.1% |

*Fragment-1 material for the solutions that were the source of the starting DCM concentrate used in these Examples.

Additional procedures involved in the solid phase, solution phase, and/or hybrid synthesis of peptides are discussed in the following U.S. provisional applications: (1) U.S. provisional application No. 60/533,655, filed Dec. 31, 2003, titled "Methods For Recovering Cleaved Peptide From A Support After Solid Phase Synthesis", in the names of inventors including Robert Orr Cain; (2) U.S. provisional application No. 60/533,691, filed Dec. 31, 2003, titled "Peptide Synthesis Using Filter Decanting", in the names of inventors including Mark A. Schwindt; (3) U.S. provisional application No. 60/533,654, filed Dec. 31, 2003, titled "Process and Systems for Peptide Synthesis", in the names of inventors including Mark A. Schwindt; and (4) U.S. provisional application No. 60/533,710, filed Dec. 31, 2003, titled "Peptide Synthesis and Deprotection Using a Cosolvent", in the names of inventors including Mark A. Schwindt.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

The invention claimed is:

1. A method of obtaining a peptide, comprising steps of:
   a. synthesizing a peptide intermediate having one or more side chain protecting groups, wherein the peptide intermediate can be used for synthesis of enfuvirtide and is selected from the group consisting of YTSLIHSL (SEQ ID NO:2), YTSLIHSLIEESQNQ (SEQ ID NO:3), YTSLIHSLIEESQNQQ (SEQ ID NO:4), YTSLIHSLIEESQNQQEK (SEQ ID NO:5), IEESQNQ (SEQ ID NO:6), IEESQNQQ (SEQ ID NO:7), QEKNEQELLELDKWASLWNW (SEQ ID NO:8), QEKNEQELLELDKWASLWNWF (SEQ ID NO:9), EKNEQEL (SEQ ID NO: 10), EKNEQELLEL (SEQ ID NO: 11), EKNEQELLELDKWASLWNWF (SEQ ID NO: 12), NEQELLELDKWASLWNW (SEQ ID NO:13), NEQELLELDKWASLWNWF (SEQ ID NO: 14), LELDKWASLWNW (SEQ ID NO: 15), LELDKWASLWNWF (SEQ ID NO: 16), DKWASLWNW (SEQ ID NO: 17), DKWASLWNWF (SEQ ID NO: 18), and EKNEQELLELDKWASLWNW (SEQ ID NO:19);
   b. providing a solvent to the peptide intermediate to form a peptide intermediate composition; and
   c. providing a precipitating agent in an amount sufficient to precipitate the peptide intermediate from the peptide intermediate composition, wherein the precipitating agent comprises an alcohol having three or more carbon atoms.

2. The method according to claim 1 wherein the step of providing a precipitating agent comprises providing a secondary or tertiary alcohol having three or more carbon atoms.

3. The method according to claim 1 wherein the step of providing a precipitating agent comprises providing a precipitating agent in an amount in the range of 5 to 8 volumes of precipitating agent per volume of peptide intermediate composition.

4. The method according to claim 3 wherein the step of providing a precipitating agent comprises providing a precipitating agent in an amount in the range of 6.5 to 7.5 volumes of precipitating agent per volume of peptide intermediate composition.

5. The method according to claim 1 wherein the step of synthesizing a peptide intermediate having one or more side chain protecting groups comprises synthesizing the peptide intermediate via solid phase peptide synthesis.

6. The method according to claim 5 further comprising the step of cleaving the peptide intermediate from a solid support prior to the step of providing a precipitating agent to precipitate the peptide intermediate.

7. The method according to claim 1 wherein the step of synthesizing a peptide intermediate having one or more side chain protecting groups comprises synthesizing the peptide intermediate via solution phase peptide synthesis.

8. The method according to claim 1 wherein the step of synthesizing a peptide intermediate having one or more side chain protecting groups comprises synthesizing the peptide intermediate via hybrid solid phase/solution phase peptide synthesis.

9. The method according to claim 1 wherein the step of synthesizing a peptide intermediate having one or more side chain protecting groups comprises synthesizing a fully protected peptide intermediate.

10. The method according to claim 1 wherein the step of synthesizing a peptide intermediate comprises synthesizing the peptide intermediate identified in SEQ ID NO: 3.

11. The method according to claim 1 wherein the step of providing a precipitating agent is carried out with agitation of less than 2.5 m/s.

12. The method according to claim 11 wherein the step of precipitating the peptide is carried out with agitation in the range of 0.25 to 2.5 m/s.

13. The method according to claim 12 wherein the step of precipitating the peptide is carried out with agitation in the range of 0.4 to 2 m/s.

14. The method according to claim 1 comprising a step of collecting the precipitate.

15. The method according to claim 1 wherein the step of providing a precipitating agent comprises providing isopropyl alcohol.

16. The method according to claim 1 wherein the step of providing a solvent to the peptide intermediate to form a peptide intermediate composition in the form of an emulsion.

17. The method according to claim 14 wherein the step of collecting the precipitate is achieved by filtration of the mixture.

18. A method of obtaining a peptide, comprising the steps of:

a. synthesizing a peptide intermediate having one or more side chain protecting groups, wherein the peptide intermediate can be used for synthesis of enfuvirtide and is selected from the group consisting of YTSLIHSL (SEQ ID NO:2), YTSLIHSLIEESQNQ (SEQ ID NO:3), YTSLIHSLIEESQNQQ (SEQ ID NO:4), YTSLIHSLIEESQNQQEK (SEQ ID NO:5), IEESQNQ (SEQ ID NO:6), IEESQNQQ (SEQ ID NO:7), QEKNEQELLELDKWASLWNW (SEQ ID NO:8), QEKNEQELLELDKWASLWNWF (SEQ ID NO:9), EKNEQEL (SEQ ID NO: 10), EKNEQELLEL (SEQ ID NO: 11), EKNEQELLELDKWASLWNWF (SEQ ID NO: 12), NEQELLELDKWASLWNW (SEQ ID NO:13), NEQELLELDKWASLWNWF (SEQ ID NO: 14), LELDKWASLWNW (SEQ ID NO: 15), LELDKWASLWNWF (SEQ ID NO: 16), DKWASLWNW (SEQ ID NO: 17), DKWASLWNWF (SEQ ID NO: 18), and EKNEQELLELDKWASLWNW (SEQ ID NO:19);

b. providing a solvent to the peptide intermediate to form a peptide intermediate composition in the form of an emulsion; and c. providing a precipitating agent in an amount sufficient to precipitate the peptide intermediate from the peptide intermediate composition, wherein the precipitating agent comprises an alcohol having three or more carbons.

* * * * *

```
                        SEQUENCE LISTING

<160> NUMBER OF SEQ ID NOS: 19

<210> SEQ ID NO 1
<211> LENGTH: 36
<212> TYPE: PRT
<213> ORGANISM: Human immunodeficiency virus

<400> SEQUENCE: 1

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 2
<211> LENGTH: 8
<212> TYPE: PRT
<213> ORGANISM: Artificial Sequence
<220> FEATURE:
<223> OTHER INFORMATION: Chemically synthesized peptide fragment

<400> SEQUENCE: 2

Tyr Thr Ser Leu Ile His Ser Leu
1               5

<210> SEQ ID NO 3
<211> LENGTH: 15
<212> TYPE: PRT
<213> ORGANISM: Artificial Sequence
<220> FEATURE:
<223> OTHER INFORMATION: Chemically synthesized peptide fragment

<400> SEQUENCE: 3

Tyr Thr Ser Leu Ile His Ser Leu Ile Glu Glu Ser Gln Asn Gln
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Chemically synthesized peptide fragment

<400> SEQUENCE: 4

Tyr Thr Ser Leu Ile His Ser Leu Ile Glu Glu Ser Gln Asn Gln Gln
1               5                   10                  15

<210> SEQ ID NO 5
<211> LENGTH: 18
<212> TYPE: PRT
```

```
<213> ORGANISM: Artificial Sequence
<220> FEATURE:
<223> OTHER INFORMATION: Chemically synthesized peptide fragment

<400> SEQUENCE: 5

Tyr Thr Ser Leu Ile His Ser Leu Ile Glu Glu Ser Gln Asn Gln Gln
1               5                   10                  15

Glu Lys

<210> SEQ ID NO 6
<211> LENGTH: 7
<212> TYPE: PRT
<213> ORGANISM: Artificial Sequence
<220> FEATURE:
<223> OTHER INFORMATION: Chemically synthesized peptide fragment

<400> SEQUENCE: 6

Ile Glu Glu Ser Gln Asn Gln
1               5

<210> SEQ ID NO 7
<211> LENGTH: 8
<212> TYPE: PRT
<213> ORGANISM: Artificial Sequence
<220> FEATURE:
<223> OTHER INFORMATION: Chemically synthesized peptide fragment

<400> SEQUENCE: 7

Ile Glu Glu Ser Gln Asn Gln Gln
1               5

<210> SEQ ID NO 8
<211> LENGTH: 20
<212> TYPE: PRT
<213> ORGANISM: Artificial Sequence
<220> FEATURE:
<223> OTHER INFORMATION: Chemically synthesized peptide fragment

<400> SEQUENCE: 8

Gln Glu Lys Asn Glu Gln Glu Leu Leu Glu Leu Asp Lys Trp Ala Ser
1               5                   10                  15

Leu Trp Asn Trp
            20

<210> SEQ ID NO 9
<211> LENGTH: 21
<212> TYPE: PRT
<213> ORGANISM: Artificial Sequence
<220> FEATURE:
<223> OTHER INFORMATION: Chemically synthesized peptide fragment

<400> SEQUENCE: 9

Gln Glu Lys Asn Glu Gln Glu Leu Leu Glu Leu Asp Lys Trp Ala Ser
1               5                   10                  15

Leu Trp Asn Trp Phe
            20

<210> SEQ ID NO 10
<211> LENGTH: 7
<212> TYPE: PRT
<213> ORGANISM: Artificial Sequence
<220> FEATURE:
<223> OTHER INFORMATION: Chemically synthesized peptide fragment

<400> SEQUENCE: 10
```

```
Glu Lys Asn Glu Gln Glu Leu
1               5

<210> SEQ ID NO 11
<211> LENGTH: 10
<212> TYPE: PRT
<213> ORGANISM: Artificial Sequence
<220> FEATURE:
<223> OTHER INFORMATION: Chemically synthesized peptide fragment

<400> SEQUENCE: 11

Glu Lys Asn Glu Gln Glu Leu Leu Glu Leu
1               5                   10

<210> SEQ ID NO 12
<211> LENGTH: 20
<212> TYPE: PRT
<213> ORGANISM: Artificial Sequence
<220> FEATURE:
<223> OTHER INFORMATION: Chemically synthesized peptide fragment

<400> SEQUENCE: 12

Glu Lys Asn Glu Gln Glu Leu Leu Glu Leu Asp Lys Trp Ala Ser Leu
1               5                   10                  15

Trp Asn Trp Phe
            20

<210> SEQ ID NO 13
<211> LENGTH: 17
<212> TYPE: PRT
<213> ORGANISM: Artificial Sequence
<220> FEATURE:
<223> OTHER INFORMATION: Chemically synthesized peptide fragment

<400> SEQUENCE: 13

Asn Glu Gln Glu Leu Leu Glu Leu Asp Lys Trp Ala Ser Leu Trp Asn
1               5                   10                  15

Trp

<210> SEQ ID NO 14
<211> LENGTH: 18
<212> TYPE: PRT
<213> ORGANISM: Artificial Sequence
<220> FEATURE:
<223> OTHER INFORMATION: Chemically synthesized peptide fragment

<400> SEQUENCE: 14

Asn Glu Gln Glu Leu Leu Glu Leu Asp Lys Trp Ala Ser Leu Trp Asn
1               5                   10                  15

Trp Phe

<210> SEQ ID NO 15
<211> LENGTH: 12
<212> TYPE: PRT
<213> ORGANISM: Artificial Sequence
<220> FEATURE:
<223> OTHER INFORMATION: Chemically synthesized peptide fragment

<400> SEQUENCE: 15

Leu Glu Leu Asp Lys Trp Ala Ser Leu Trp Asn Trp
1               5                   10

<210> SEQ ID NO 16
<211> LENGTH: 13
<212> TYPE: PRT
```

-continued

```
<213> ORGANISM: Artificial Sequence
<220> FEATURE:
<223> OTHER INFORMATION: Chemically synthesized peptide fragment

<400> SEQUENCE: 16

Leu Glu Leu Asp Lys Trp Ala Ser Leu Trp Asn Trp Phe
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Chemically synthesized peptide fragment

<400> SEQUENCE: 17

Asp Lys Trp Ala Ser Leu Trp Asn Trp
1               5

<210> SEQ ID NO 18
<211> LENGTH: 10
<212> TYPE: PRT
<213> ORGANISM: Artificial Sequence
<220> FEATURE:
<223> OTHER INFORMATION: Chemically synthesized peptide fragment

<400> SEQUENCE: 18

Asp Lys Trp Ala Ser Leu Trp Asn Trp Phe
1               5                   10

<210> SEQ ID NO 19
<211> LENGTH: 19
<212> TYPE: PRT
<213> ORGANISM: Artificial Sequence
<220> FEATURE:
<223> OTHER INFORMATION: Chemically synthesized peptide fragment

<400> SEQUENCE: 19

Glu Lys Asn Glu Gln Glu Leu Leu Glu Leu Asp Lys Trp Ala Ser Leu
1               5                   10                  15

Trp Asn Trp
```